United States Patent [19]

Frank et al.

[11] 4,429,569
[45] Feb. 7, 1984

[54] DEVICE FOR TESTING THE SHORE-HARDNESS OF RUBBER-LIKE ARTICLES

[75] Inventors: Erich Frank, Bad König; Walter Scheuermann, Erbach; Georg Volk, Breuberg, all of Fed. Rep. of Germany

[73] Assignee: Metzeler Kautschuk GmbH, Munich, Fed. Rep. of Germany

[21] Appl. No.: 367,896

[22] Filed: Apr. 13, 1982

[30] Foreign Application Priority Data

Apr. 18, 1981 [DE] Fed. Rep. of Germany ....... 3115814

[51] Int. Cl.³ .............................................. G01N 3/42
[52] U.S. Cl. ..................................................... 73/81
[58] Field of Search .................. 73/78, 79, 81, 82, 83, 73/85

[56] References Cited

U.S. PATENT DOCUMENTS 2,912,105  11/1959  Allured et al. .......................... 73/83
4,111,039  9/1978  Yamawaki .............................. 73/81

*Primary Examiner*—S. Clement Swisher
*Attorney, Agent, or Firm*—Herbert L. Lerner; Laurence A. Greenberg

[57] ABSTRACT

Device for testing the shore-hardness of rubber-like (elastomer) bodies, particularly rubber/metal parts, comprising a measuring head with a movable penetrator which can be positioned onto the surface of the rubber-like body, a rotatable circular plate, mounting elements which hold said rubber-like bodies, which are arranged at the circumference of the circular plate, an adjustable holding arrangement for the measuring head, and an actuating device for the measuring head.

5 Claims, 2 Drawing Figures

DEVICE FOR TESTING THE SHORE-HARDNESS OF RUBBER-LIKE ARTICLES

BACKGROUND OF THE INVENTION

1. Field of the Invention

The invention relates to a device for testing the Shore-hardness of rubber-like (elastomer) articles, particularly articles having rubber/metal parts.

2. Description of the Prior Art

At the completion of manufacture of rubber/metal parts, all finished parts must be tested for hardness at the final inspection. The sorting of the good from the bad is a customer requirement, which additionally must be certified in writing.

The conventional instruments used to date for hardness-testing rubber-like bodies according to Shore A and Shore D have a measuring head with a movable penetrator element, which is placed onto the surface of the body which is to be tested. However, this manual operation is laborious and cumbersome, and also boring for the operator, so that it is not suited for a continuous final inspection.

SUMMARY OF THE INVENTION

An object of the invention is to provide a device for the continuous, uniform testing, almost fully automatically of the Shore-hardness of rubber-like bodies produced by mass production, wherein the mentioned disadvantages are eliminated.

With the foregoing and other objects in view, there is provided in accordance with the invention a device for testing the Shore-hardness of rubber-like bodies comprising (a) a measuring head with a movable penetrator which can be positioned onto the surface of the rubber-like body for testing the Shore-hardness.

(b) a rotatable circular plate, (c) a plurality of spaced mounting elements disposed at the circumference of the circular plate for holding said rubber-like bodies during rotation of the circular plate to bring each said body to the measuring head for testing and away from the head after testing, (d) an adjustable mounting arrangement which is movable to adapt to rubber-like bodies of different dimensions, for holding the measuring head in position adjacent the rubber-like body for testing Shore-hardness, and (e) an actuating device connected to the measuring head for actuating said movable penetrator.

Other features which are considered as characteristic for the invention are set forth in the appended claims.

Although the invention is illustrated and described herein as embodied in a device for testing the Shore-hardness of rubber-like article, it is nevertheless not intended to be limited to the details shown, since various modifications may be made therein without departing from the spirit of the invention and within the scope and range of equivalents of the claims.

BRIEF DESCRIPTION OF THE DRAWINGS

The invention, however, together with additional objects and advantages thereof will be best understood from the following description when read in connection with the accompanying drawings in which.

DETAILED DESCRIPTION OF THE INVENTION

Figures 1, 2:
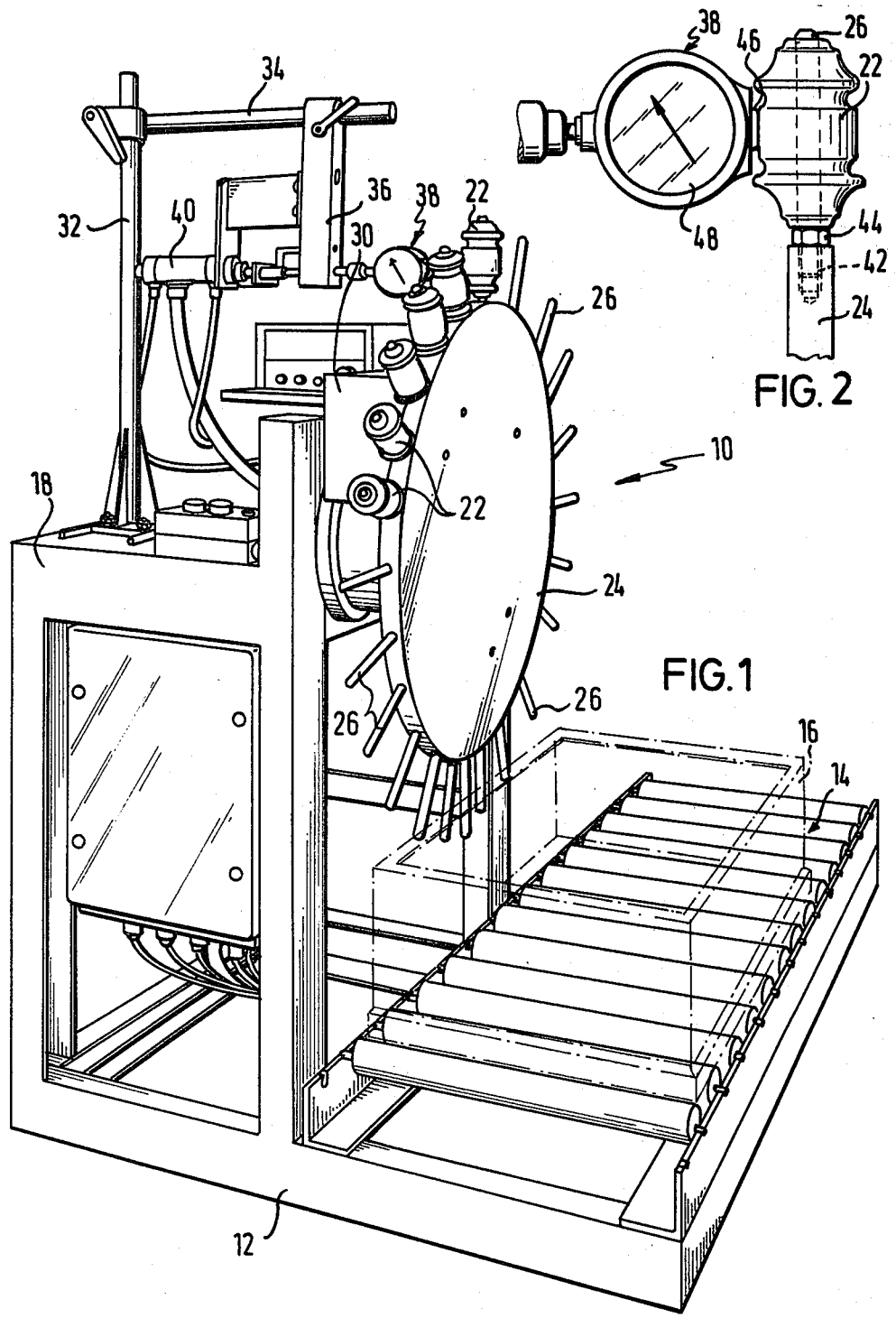
FIG. 1 is a perspective view of the device for the automatic testing of the Shore-hardness of hollow rubber-like bodies.
FIG. 2 is a view of the measuring head and a rubber-like article in an enlarged scale.

The device for testing the Shore-hardness of rubber-like (elastomer) bodies, particularly rubber/metal parts, comprises a measuring head with a movable penetrator which can be positioned onto the surface of the rubber-like body, a rotatable circular plate, mounting elements which hold said rubber-like bodies, which are arranged at the circumference of the circular plate, an adjustable holding arrangement for the measuring head, and an actuating device for the measuring head.

The individual rubber-like articles, for example, rubber/metal parts, are held by holding elements, which are disposed at the circumference of a rotatable circular plate. This circular plate moves intermittently and transports the holding elements, and thereby also the rubber-like bodies up to a measuring head, which is automatically actuated, to position the movable penetrator element onto the surface of the rubber-like body. The measurement is then performed in the conventional manner, and its result, if required is stored and produced by a data processing system.

At the following intermittent rotation of the circular plate, the tested rubber-like body is moved from the measuring station and the next rubber-like body is moved into the measuring position, so that it can be tested.

The holding of the rubber-like bodies at the circumference of the circular plate can be effected, for example, by clamping elements. If hollow rubber-like articles are to be tested, as is often required for rubber/metal parts, the holding elements are preferably made in the form of pins, which protrude radially from the circumference of a circular disc which is arranged in a vertical plane. In this case the hollow rubber-like bodies need only be pushed onto these pins, which then transport them to the measuring head. During the rotation of the circular plate, the rubber-like bodies finally reach a position, when they slide down from the pins by their own weight, for example, into a container, which can be automatically transported away.

If a hardness value is found at a certain rubber-body which lies outside of the specified tolerance range, an alarm signal can be generated, for example, so that this rubber-like article can be manually withdrawn from the production lot. This system operates almost automatically, and can simultaneously also give a print-out of the test result, resulting in the desired complete inspection of the whole production with low labor cost.

The invention will be further explained in the following with the aid of typical embodiments and referring to the accompanying schematic drawings.

As shown in FIG. 1, the device for testing the Shore-hardness of rubber-like bodies is generally designated 10, and has a rectangular base 12, on which at one side a roller conveyor 14 for the container 16 is arranged, and on the other side, is a square-shaped frame 18. A circular plate 24, vertically supported on the frame 18, can rotate around a horizontal axis. Intermittent rotation of the circular plate 24 may be effected by suitable drive or rotating means 30 such as a motor and gears with timing connected to the circular plate. Outward protruding pins 26 are provided at the circumference of said circular plate, onto which pins the hollow rubber articles 22 can be placed.

A vertical rod 32 is mounted on the upper surface of frame 18, with a vertical carrier 36 for the measuring head 38 fastened to the rod by means of a crossbar 34. The connections between the frame 18, the rod 32, the crossbar 34 and the carrier 36 and the measuring head 38 are adjustable or movable, so that the position of the measuring head 38 can be adapted to the dimensions of varied rubber articles 22.

The measuring head 38 is provided with an actuating device 40 which actuates the penetrating element 46, which can be seen in FIG. 2. Furthermore, the measuring head 38 has a conventional indicating display with a scale 48.

The digital measuring result determined by the measuring head 38 is transfered to a computer print-out through a digital/analog converter. This programmed computer controls the whole measuring operation, whereby cycle, measuring time, tolerance range etc. are specified. The result of the measurement for each rubber-body is also digitally displayed.

An impermissible deviation of the measured value from a specified nominal value is recognized by the printing computer, which compares the analog result of the measurement with the nominal value, and stops the device 10 if the specified tolerance limit is exceeded and simultaneously emits an acoustic signal, so that the rubber article which is outside the tolerance can be removed by hand from the measuring station. In practice this presents no problem because generally the number of rejects is in the range of one reject in a thousand articles tested. The measured value is digitally displayed, but generally the printer shows only the running number of rejects.

In FIG. 2, the edge of the circular plate 24 provided at its circumference with a threaded hole 42 is shown. The threaded part of the pin 26 is screwed into the threaded hole 42, and secured by a nut 44.

The outer diameter of the pin 26 corresponds approximately to the inner diameter of the hollow rubber-article 22, so that the pins 26 serve simultaneously as a gauge for the inner diameter of the rubber articles 22. The pins 26 can be easily exchanged, if they are to be adapted for rubber articles with another diameter.

The contacting of the penetrating element 46 of the measuring head 38 on the outer surface of the rubber article 22 can be seen in FIG. 2. By a suitable adjustment of rod 32, crossbar 34 and carrier 36, the measuring head 38 can be set to any desired contact angle with the surface of the rubber article 22.

At the rotation of the circular plate 24, the individual pins 26 are brought step-by-step to the measuring position sequentially, and thereby also the individual rubber articles 22, so that their hardness can be determined. Finally, at a further rotation of the circular plate 24, the rubber articles slide-off from the pins 26, and fall downward into the container 16 on the roller conveyor 14, so that they can be transported further on when the container 16 is full.

We claim:

1. Device for testing the Shore-hardness of rubber-like bodies comprising
  (a) a measuring head with a movable penetrator which can be positioned onto the surface of the rubber-like body for testing the Shore-hardness,
  (b) a rotatable circular plate disposed in a vertical plane,
  (c) a plurality of spaced mounting elements dispoed at the circumference of the circular plate for holding said rubber-like bodies during rotaton of the circular plate to bring each said body to the measuring head for testing and away from the head after testing,
  (d) an adjustable mounting arrangement which is movable to adapt to rubber-like bodies of different dimensions, for holding the measuring head in position adjacent the rubber-like body for testing Shore-hardness, and
  (e) an actuating device connected to the measuring head for actuating said movable penetrator, wherein the mounting elements are pins and the rubber-like bodies are hollow, and where said pins for holding the hollow rubber-like bodies protrude radially from the circumference of the circular plate.

2. Device according to claim 1, wherein the outer diameter of the pins is somewhat smaller than the inner diameter of the hollow rubber-like bodies to permit easy placement on the pins and ready removal therefrom.

3. Device for testing the Shore-hardness of rubber-like bodies comprising
  (a) a measuring head with a movable penetrator which can be positioned onto the surface of the rubber-like body for testing the Shore-hardness,
  (b) a rotatable circular plate disposed in a vertical plane,
  (c) a plurality of spaced mounting elements disposed at the circumference of the circular plate for holding said rubber-like bodies during rotation of the circular plate to bring each said body to the measuring head for testing and away from the head after testing,
  (d) an adjustable mounting arrangement which is movable to adapt to rubber-like bodies of different dimensions, for holding the measuring head in position adjacent the rubber-like body for testing Shore-hardness, and
  (e) an actuating device connected to the measuring head for actuating said movable penetrator, wherein the adjustable mounting arrangement comprises a vertical rod, a crossbar adjustably connected to the vertical rod and movable vertically, and a vertical carrier for the measuring head adjustably connected to the crossbar and movable horizontally.

4. Device according to claim 1, wherein the pins mounted on the circumference of the circular plate are readily removable and are exchangeable for pins of different dimensions.

5. Device according to claim 4, wherein the pins have threaded ends, and wherein threaded holes are provided at the circumference of the circular plate for the insertion of the threaded ends of the pins.

* * * * *